(12) United States Patent  
Raynor (10) Patent No.: US 7,541,176 B2  
(45) Date of Patent: Jun. 2, 2009

(54) FLUORESCENCE BIOSENSOR

(75) Inventor: Jeffrey Raynor, Edinburgh (GB)

(73) Assignee: STMicroelectronics (Research & Development) Limited, Marlow-Buckinghamshire (GB)

( * ) Notice: Subject to any disclaimer, the term of this patent is extended or adjusted under 35 U.S.C. 154(b) by 0 days.

(21) Appl. No.: 11/677,765

(22) Filed: Feb. 22, 2007

(65) Prior Publication Data

US 2007/0207536 A1    Sep. 6, 2007

(30) Foreign Application Priority Data

Feb. 23, 2006    (EP) .................... 06250958

(51) Int. Cl.
*C12M 1/34*    (2006.01)
(52) U.S. Cl. .................................. 435/287.2
(58) Field of Classification Search .......... 435/287.2; 422/50, 82.05, 82.07, 82.08
See application file for complete search history.

(56) References Cited

U.S. PATENT DOCUMENTS

| 3,655,987 | A |   | 4/1972 | Hinds ..................... 250/206 |
| 4,688,017 | A | * | 8/1987 | Huebner et al. ............. 341/137 |
| 5,715,049 | A |   | 2/1998 | Ohsuka et al. .............. 356/215 |
| 5,998,152 | A | * | 12/1999 | Lynch et al. ................ 435/7.1 |

FOREIGN PATENT DOCUMENTS

| DE | 4420572 | 12/1995 |
| JP | 2000205951 | 7/2000 |

* cited by examiner

*Primary Examiner*—Ann Y Lam
(74) *Attorney, Agent, or Firm*—Lisa K. Jorgenson; Allen, Dyer, Doppelt, Milbrath & Gilchrist, P.A.

(57) ABSTRACT

A fluorescence detector includes a light source being positioned so that in use, radiation emitted therefrom falls on one or more fluorescing species, and a photodetector being switchably connectable between a charge integrator device and a charge disposal device. The photodetector is positionable to detect fluorescent radiation from the fluorescing species. A controller communicates with the light source and the photodetector, and is operable in a cyclic manner to activate the light source to emit radiation and connect the photodetector to the charge disposal device for a first period of time, and connect the photodetector to the charge integrator device for a second period of time after the first period. The charge integrator device is not reset from one cycle to the next.

10 Claims, 6 Drawing Sheets

FLUORESCENCE BIOSENSOR

FIELD OF THE INVENTION

The present invention relates to sensors, and in particular, to a fluorescence biosensor.

BACKGROUND OF THE INVENTION

Biosensors are analytical tools that detect the presence of a chemical or biochemical species in a complex mixture by combining the molecular recognition properties of biological macromolecules (e.g., enzymes, antibodies, DNA or even whole cells) with signal transduction mechanisms (e.g., optical or electrochemical) that couple ligand bindings with readily detectable physical changes.

The optical signal transduction mechanisms employed by biosensors are based on absorption spectroscopy (ultraviolet (UV) to deep infrared (IR)), Raman or fluorescence spectroscopy. Fluorescence spectroscopy provides a particularly important detection mechanism because a number of biological species (including the green fluorescent protein (GFP), nucleic acids and flavine nucleotides) are naturally fluorescent. In addition, biological species that are not naturally fluorescent may be chemically bound to fluorescent molecules (known as labels).

To increase analytical throughput, an analytical process should be capable of simultaneously detecting a number of different species. Biosensor arrays achieve this by assembling a large number of different biological macromolecules (each of which contains a recognition site for a given biological species, with such species being known henceforth as an analyte) into densely packed arrays of unique sensor elements.

Biosensor arrays have three main operational mechanisms, namely labeled analyte pooling (used in DNA and RNA hybridization assays), sandwich assays (used for antibody recognition) and direct assays.

Figure 1:
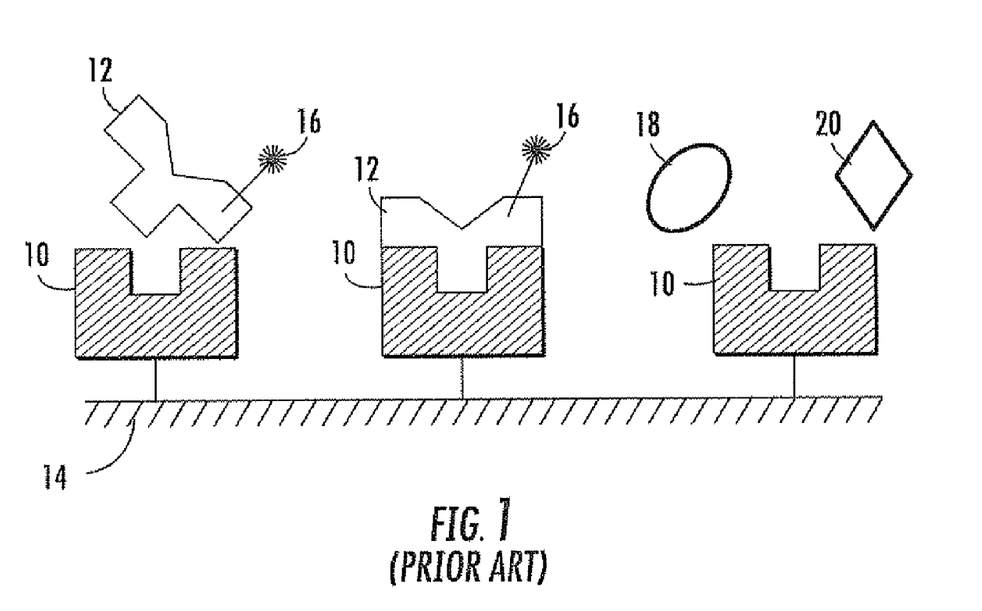
FIG. 1 is a block diagram of one of the operating mechanisms of a fluorescence biosensor according to the prior art.

Referring to FIG. 1, during labeled analyte pooling a biological macromolecule 10 specific for an analyte 12 is immobilized on a solid support 14. A sample (containing an analyte 12) is mixed with a solution of a fluorescent label 16 that binds to the analyte 12 therein. The sample is then introduced to the biosensor array and the analyte 12 therein is bound to the biological macromolecule 10 specific therefore. Other species 18, 20 in the sample that are not of analytical interest (and for which there are no biological macromolecules immobilized on the solid support 14) remain in free solution.

The support 14 is then washed with a cleaning solution (not shown) and any unbound species in the sample are flushed therefrom, leaving the fluorescently labeled analyte 12 bound to the support 14. The fluorescently labeled analyte 12 fluoresces when exposed to radiation (e.g., from an IR laser) and the resulting fluorescent pattern of the biosensor array acts as a biochemical fingerprint that can be readily imaged.

Figure 2:
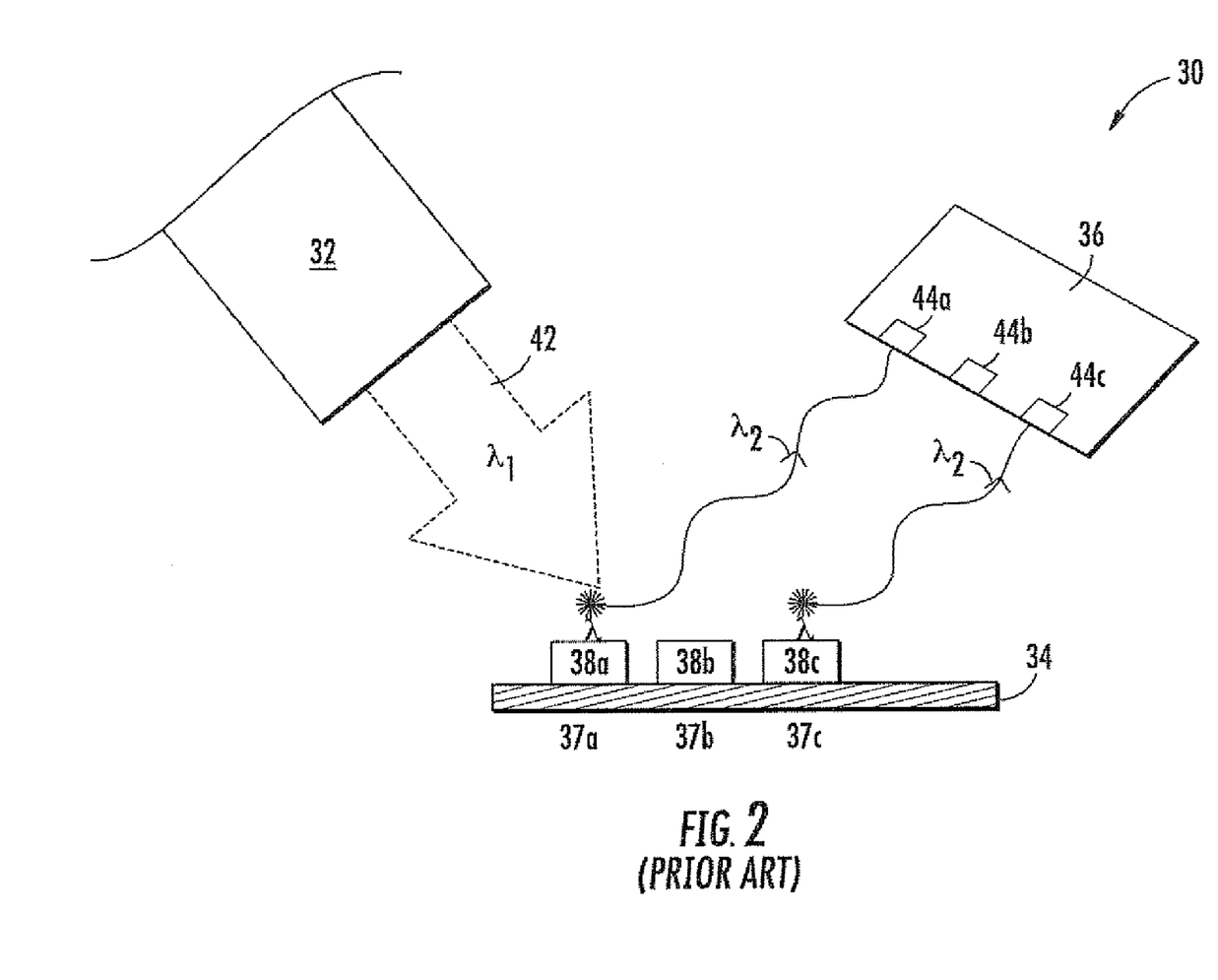
FIG. 2 is a block diagram of a generic conventional fluorescence biosensor according to the prior art.

Referring to FIG. 2, a fluorescence biosensor 30 typically comprises a stimulating light source 32, a substrate 34 and a photodetector 36. The substrate 34 comprises a plurality of sensor elements 37a, 37b and 37c each of which comprises an immobilized biological macromolecule 38a, 38b and 38c specific for a particular analyte of interest. While FIG. 2 shows the photodetector 36 disposed remotely from the substrate 34, nonetheless, it will be appreciated that this arrangement is not essential and the substrate 34 could alternatively be configured to house both the photodetector 36 and the sensor elements 37a, 37b and 37c.

Using, for example, the above-described labeled analyte pooling scheme, analytes 40a and 40c in a sample have fluorescent labels bound thereto. When the sample (not shown) is introduced to the substrate 34, the labeled analytes 40a and 40c bind to the appropriate macromolecule 38a and 38c. However, if an analyte that binds to a particular macromolecule 38b is not present in the sample, the corresponding sensor element 37b remains free of labeling.

The light source 32 emits light 42 of wavelength $\lambda^1$, which is a stimulating wavelength for the fluorescent labels (bound to the analytes 40a and 40c). The light source 32 is positioned so that the light 42 it emits falls upon the sensor elements 37a, 37b and 37c (and any fluorescently labeled analytes bound thereto). It will be appreciated that there may be some additional optical elements (e.g., lens, lightguide, etc.) disposed between the light source 32 and the sensor elements 37a, 37b and 37c. It will also be appreciated that the light source 32 may alternatively scan the array of sensor elements 37a, 37b and 37c. The light 42 stimulates the fluorescent labels bound to the analytes 40a and 40c to emit radiation of wavelength $\lambda^2$ ($\lambda^1 < \lambda^2$).

The photodetector 36 comprises a plurality of pixels 44a, 44b and 44c, each of which is positioned to detect the radiation emitted from a given sensor element 37a, 37b and 37c. As before, it will be appreciated that there may be some additional optical elements (e.g. lens, a light guide, etc.) disposed between the sensor elements 37a, 37b and 37c and the photodetector 36. It will also be appreciated that the photodetector 36 may alternatively scan the array of sensor elements 37a, 37b and 37c.

While the biochemistry of immobilizing biological macromolecules, etc. is relatively well established, one of the main problems which remains to be addressed arises because the radiation $\lambda^2$ emitted from the fluorescently labeled analytes 40a and 40c is very weak compared to the radiation 42 emitted by the light source 32.

There are a number of devices currently on the market for analyzing biological samples. For example, the Agilent 2100 bioanalyzer uses microfluidic technology to enable electrophoretic separation of biological components (detected by fluorescence) and flow cytometric analysis of cell fluorescence parameters. The Agilent 2100 bioanalyzer uses a laser (as a stimulating light source) to scan the relevant biological components and a photomultiplier tube to detect the weak fluorescence signal emitted therefrom.

Unfortunately, prior art systems such as the Agilent 2100 bioanalyzer are typically large, very expensive and not amenable to miniaturization. In addition, the process of optimizing the focus of the stimulating light source (to compensate for tilting of the specimen and/or non-flat surfaces) can be quite complicated.

Finally, since the Agilent 2100 bioanalyzer scans each sensor element (e.g., DNA binding site) serially, the scanning time of the bioanalyzer is dependent on the number of sensor elements on a substrate. Consequently, if a substrate contains a number of sensor elements (to detect multiple different analytes) the scanning time of the Agilent 2100 bioanalyzer may be quite long.

At present, fluorescent biosensor typically use charge coupled devices (CCDs) or complementary metal oxide (CMOS) cameras as photodetectors. Sometimes dichroic mirrors are used to separate the radiation from the stimulating light source (known as stimulating radiation) from the radiation emitted by the fluorescent labels (known as fluorescent radiation) on the basis of the difference in their wavelengths (i.e., $\lambda_{stim} < \lambda_{fluor}$). However, these wavelength discrimination systems are typically large and expensive.

One way of avoiding the problem of the large size of such wavelength discrimination systems is to perform temporal discrimination by synchronizing the operation of the biosensor's stimulating light source and photodetector. To illustrate this point, FIG. 3 shows the relative timing of:

(a) an activation signal (STIM) for a biosensor's stimulating light source;

(b) a reset signal (RESET) of the biosensor's CCD/CMOS detector; and (c) a voltage (Vpd) generated in the biosensor's CCD/CMOS detector.

Figures 3A, 3B, 3C:
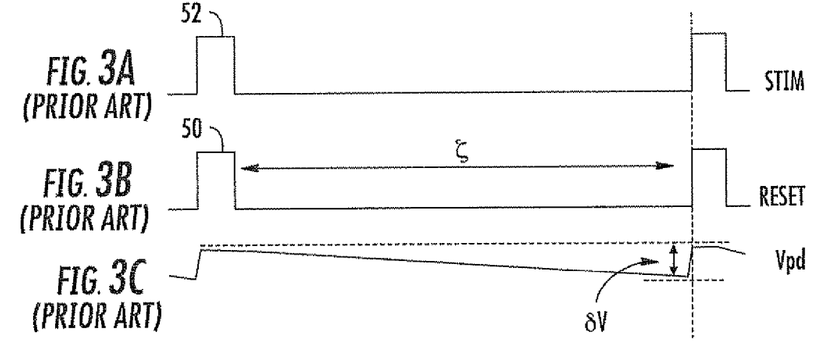
FIG. 3 a timing diagram of a three transistor (3T) pixel in the photodetector of the conventional fluorescence biosensor shown in FIG. 2.

Referring to traces (a) and (b) in FIG. 3, it can be seen that the stimulating light source is activated in a pulsating fashion, which is timed to match the timing of the reset signal. The CCD/CMOS detector is reset by a pulse 50 while the fluorescent labels are being stimulated by a pulse 52 from the stimulating light source (trace (a)). Thus, the CCD/CMOS does not start to measure radiation until after the stimulating light source pulse 52 (trace (a)) is ended and the only light present is that emitted from the fluorescent labels.

However, as the amount of light emitted by a fluorescent label is quite small, a comparatively small voltage (67V) is generated thereby in the CCD/CMOS detector during measurement time interval ($\tau$). Thus, the sensitivity of a CCD/CMOS detector to such fluorescent radiation becomes particularly important.

One way of increasing the sensitivity of a CCD/CMOS detector would be to increase the size of its pixels. As biosensor arrays comprise a small number of sensor elements compared with the number of pixels in a conventional CCD/CMOS detector, such CCD/CMOS detectors possess more than enough resolution to image the biosensor array. Consequently, there is no practical impediment to scanning biosensor arrays with such larger pixels, wherein a charge integrator circuit as depicted in FIG. 4 is particularly suitable for processing the signals acquired by such enlarged pixels.

Figure 4:
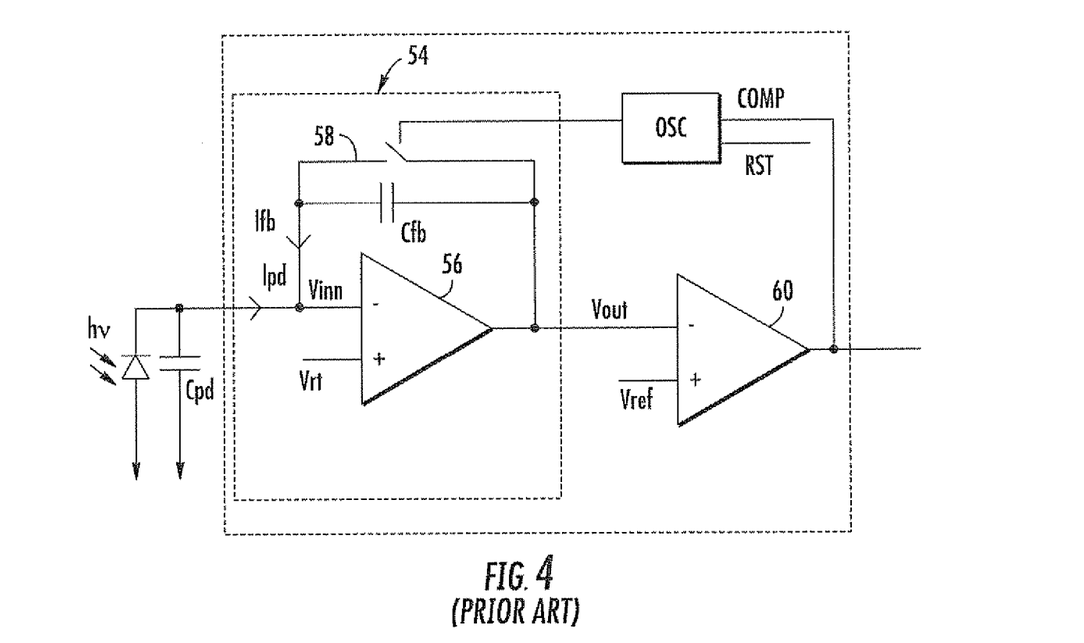
FIG. 4 is a circuit diagram of a charge integrator employed in the photodetector of the conventional fluorescence biosensor shown in FIG. 2.

Referring to FIG. 4, the charge integrator circuit 54 comprises a charge amplifier 56 connected in parallel with a feedback capacitor $C_{fb}$ and a reset switch 58. The charge integrator circuit 54 is in turn connected to a comparator 60 which permits the conversion of the analog output from the charge integrator circuit 54 into a digital value by ramping a reference signal ($V_{ref}$) (from a digital to analog converter (DAC), for example) and using the comparator's 60 output to store the resulting digital value.

The output from the charge integrator circuit 54 may also be converted to a digital signal by connecting an analog to digital converter (ADC) to the charge integrator circuit 54 (instead of the comparator 60) Alternatively, the configuration shown in FIG. 4 (with the comparator 60 connected to the output of the charge integrator circuit 54) may be used with the reference signal ($V_{ref}$) held constant and measuring the amount of time for the output from the charge integrator circuit 54 to reach the level of the reference signal (i.e., until $V_{out}=V_{ref}$).

SUMMARY OF THE INVENTION

A first aspect of the invention is to provide a fluorescence detector comprising a light source positioned so that in use, radiation emitted therefrom falls on one or more fluorescing species, and a photodetector being switchably connectable between a charge integrating means or device and a charge disposal means or device. The photodetector may be positioned to detect fluorescent radiation from the fluorescing species. The fluorescence detector may further comprise a controller in communication with the light source and the photodetector.

The controller may be operable in a cyclic manner to activate the light source to emit radiation and connect the photodetector to the charge disposal device for a first period of time, and connect the photodetector to the charge integrator circuit for a second period of time after the first period. The charge integrator circuit is not reset from one cycle to the next.

The controller may be operable to connect the photodetector to the charge integrator device approximately 0.1 to 5 ns after the end of the first period.

The detector may comprise means or a circuit for reducing a charge injected into the charge integrator device by the switching of the photodetector from the charge disposal device to the charge integrator device.

According to a second aspect, the fluorescence biosensor may comprise the fluorescence detector as discussed in the first aspect, wherein the fluorescence detector may be integrated with the fluorescing species and the fluorescing species may be a biological macromolecule.

According to a third aspect of the invention, the fluorescence biosensor may comprise the fluorescence detector as discussed in the first aspect, wherein the fluorescence detector may be integrated with the fluorescing species and the fluorescing species may be a fluorescently labelled biological macromolecule.

According to a fourth aspect of the invention, a clinical diagnostic system comprises the fluorescence detector as discussed in the first aspect or the fluorescence biosensor according to the second or third aspects.

According to a fifth aspect of the invention, a food testing system comprises the fluorescence detector as discussed in the first aspect or the fluorescence biosensor of the second or third aspects.

According to a sixth aspect of the invention, a pharmaceutical testing system comprises the fluorescence detector of the first aspect or the fluorescence biosensor of the second or third aspects.

According to a seventh aspect of the invention there is provided a method of improving the sensitivity of a fluorescence biosensor comprising the steps of illuminating one or more fluorescent species with stimulating radiation for a first period of time, and disposing of charges generated in a photodetector by the stimulating radiation. The method may further comprise accumulating in a charge integrator over a second period of time, after the first period, the charge generated in the photodetector by fluorescent radiation emitted from the fluorescent species. These steps are cyclically repeated without resetting the charge integrator between cycles. The accumulating may be performed approximately 0.1 to 5 ns after the first period of the illuminating.

An advantage of the improved fluorescence biosensor is that there is an increased sensitivity to fluorescent radiation compared with conventional fluorescence biosensors. Consequently, the stimulating light source in the improved fluorescence biosensor does not need to stimulate fluorescent labels with as much power as conventional fluorescence biosensors. Thus, cheaper light sources can be used in the improved fluorescence biosensor compared with those of conventional fluorescence biosensors.

The fluorescence biosensor advantageously discriminates between stimulating radiation and fluorescent radiation directly on its photodetector's pixels. This eliminates the need for wavelength filtering, thereby reducing the size of the improved fluorescence biosensor and leading the way to a miniaturized Lab-on-Chip system. In addition, the removal of the need for expensive wavelength filtering, ensures that the fluorescence biosensor is cheaper to manufacture than conventional fluorescence biosensors.

BRIEF DESCRIPTION OF THE DRAWINGS

An embodiment of the invention will now be described by way of example only with reference to the accompanying figures in which.

DETAILED DESCRIPTION OF THE PREFERRED EMBODIMENTS

Figure 5:
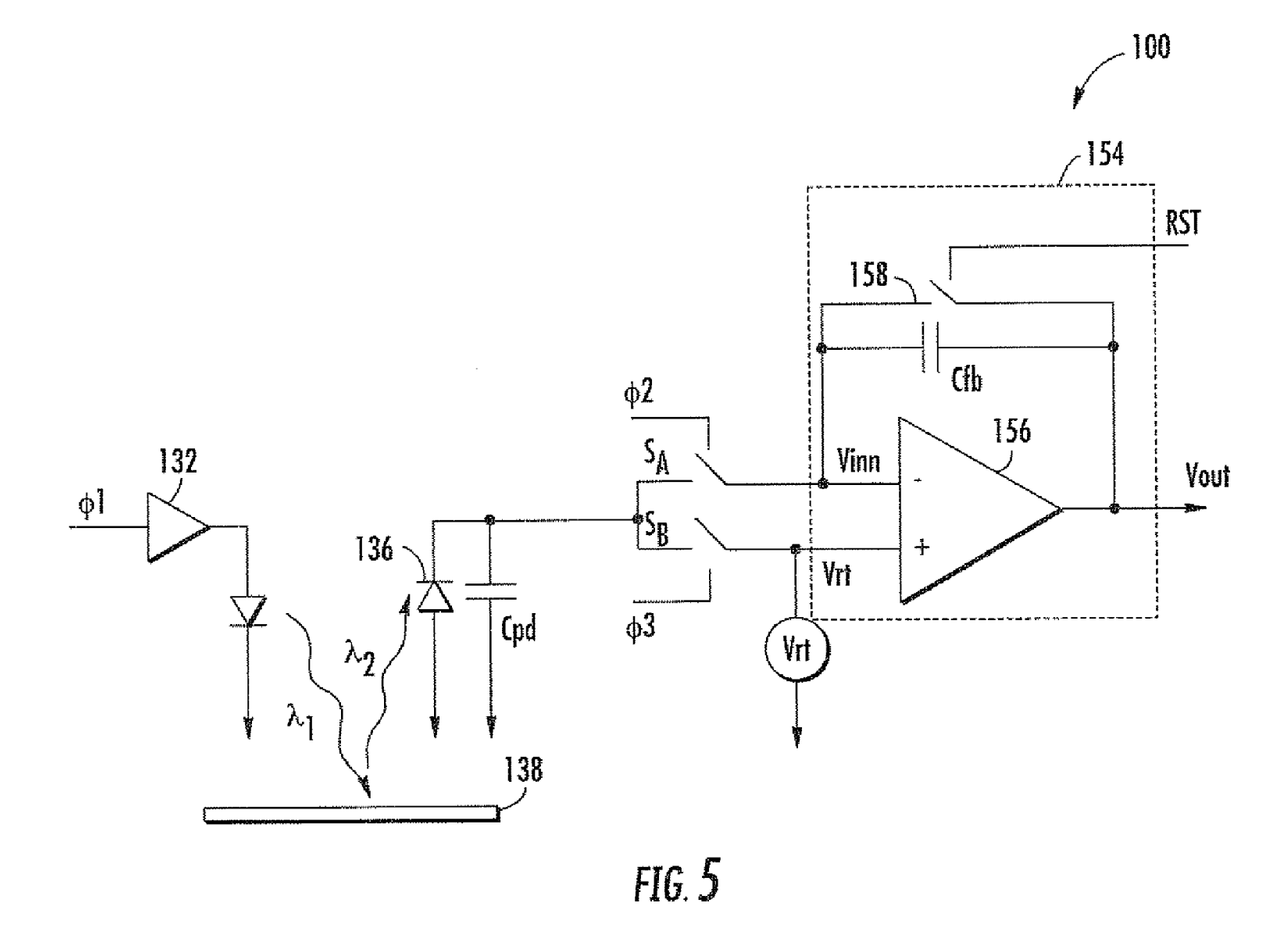
FIG. 5 is a circuit diagram of a fluorescence biosensor in accordance with a first aspect of the invention.

Referring to FIG. 5, a key feature of the fluorescence biosensor 100 is the repeated activation (by an activating signal $\phi_1$) of the stimulating light source 132 over a pre-defined period (known as the measurement period $\tau$). The radiation from the stimulating light source 132 (i.e., the stimulating radiation $\lambda_1$) stimulates the fluorescent labels 138 in the fluorescence biosensor 100 to repeatedly emit fluorescent radiation $\lambda_2$ over the measurement period $\tau$.

At the same time, the fluorescence biosensor 100 accumulates the small number of electrons produced in the biosensor's photodetector 136 by the repeated emissions of fluorescent radiation $\lambda_2$. For the sake of simplicity, the photons of the stimulating radiation $\lambda_1$ will be known as stimulating photons. Similarly, the photons of the fluorescent radiation $\lambda_2$ will be known as fluorescent photons.

By accumulating the photogenerated electrons over the duration of the measurement period $\tau$, the net photogenerated charge in the photodetector 136 is increased, thereby improving the fluorescence biosensor's 100 signal to noise performance.

Unlike prior-art systems, the fluorescence biosensor 100 uses switches $S_a$, $S_b$ (implemented, for example, by wiring NMOS and PMOS transistors in parallel with their gates driven by opposing signals $\phi_2$, $\phi_3$) to:

(a) connect/disconnect the biosensor's photodetector 136 to/from a charge integrator circuit 154 comprising a charge amplifier 156 connected in parallel with a feedback capacitor $C_{fb}$ and a reset switch RST; and (b) connect or disconnect the photodetector 136 to/from a low-impedance dump voltage $V_{rt}$ that enables the dumping of the photogenerated electrons accumulated over the duration of the measurement period $\tau$.

Figure 6:
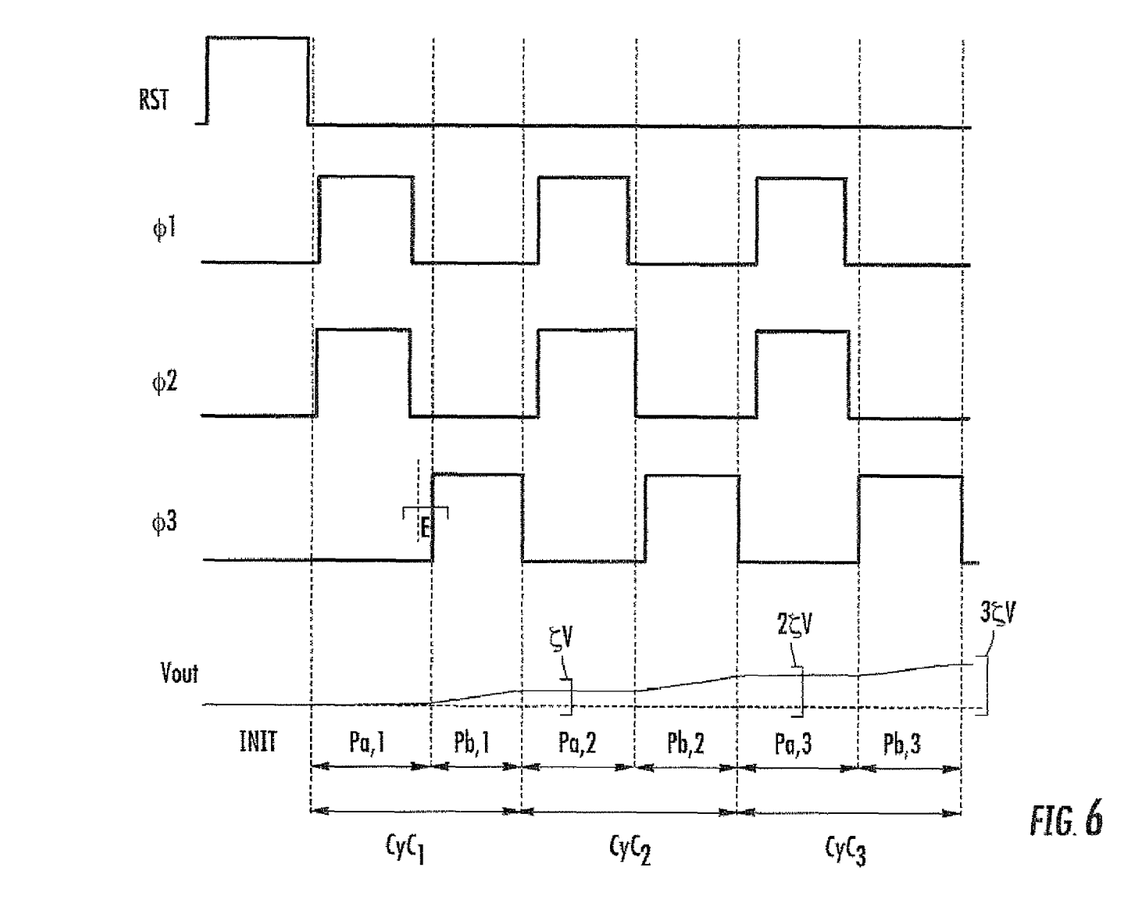
FIG. 6 is a timing diagram of the fluorescence biosensor shown in FIG. 5.

The operation of the fluorescence biosensor 100 can be best explained by examining the timing diagram depicted in FIG. 6 together with the circuit diagram of FIG. 5.

The fluorescence biosensor 100 operates in a cyclic fashion wherein each cycle comprises two phases ($p_a$ and $p_b$). FIG. 6 depicts three of these cycles, namely $Cyc_1$, $Cyc_2$ and $Cyc_3$, wherein the two phases of the first cycle are denoted by $P_{a,1}$ and $P_{b,1}$, and the two phases of the second and third cycles are denoted by $p_{a,2}$ and $p_{b,2}$, and $p_{a,3}$ and $p_{b,3}$ respectively.

Before starting the cyclic operations, the fluorescence biosensor's charge integrator 154 is reset (by a reset pulse RST) during an initialization phase INIT.

During the first phase $p_{a,1}$ of the first cycle $Cyc_1$, the stimulating light source 132 is turned on by an activating signal $\phi_1$. At the same time, a switching signal $\phi_2$ connects the photodetector 136 to the low-impedance dump voltage $V_{rt}$. This ensures that the electrons generated in the photodetector 136 by the stimulating radiation $\lambda_1$ are deposited in the dump voltage $V_{rt}$ and not the charge integrator 154.

At the end of the first phase $p_{a,1}$, the stimulating light source 132 is turned off by switching the activating signal $\phi_1$ to low. Around the same time (but not exactly the same time, as discussed below), the second switching signal $\phi_2$ is also switched low, thereby disconnecting the photodetector 136 from the dump voltage $V_{rt}$. The disconnecting process should not occur until after:

(i) the stimulating photons have been received by the photodetector 136; and (ii) the electrons generated in the photodetector 136 by the stimulating photons have been fully collected.

The fulfillment of these two conditions ensures that the only photogenerated electrons accumulated in the charge integrator 154 are those derived from the fluorescent radiation $\lambda_2$. The time necessary to achieve the first condition is relatively easy to calculate, as it is the product of the speed of light and the length of the light path in the fluorescence biosensor 100.

However, calculating the time necessary to achieve the second condition is more complex. In particular, this parameter depends on:

(a) the wavelength of the stimulating radiation $\lambda_1$, as this feature determines the penetration depth of the stimulating photons into the silicon of the photodetector 136;

(b) the depth of the semiconductor junction in the photodetector 136;

(c) the mobility of the photogenerated electrons in the silicon of the photodetector 136; and (d) the electric field applied to the photodetector 136.

As the power of the stimulating radiation $\lambda_1$ is much greater than the power of the fluorescent radiation $\lambda_2$, the number of stimulating photons is much greater than the number of fluorescent photons. Accordingly, it is very important that the charge integrator 154 should not collect charges generated by the stimulating photons (even to the point of rejecting some of the charges generated by the fluorescent photons). A typical value for the time difference $\gamma$ (not shown) between the switching low of the activating signal $\phi_1$ and the switching low of the first switching signal $\phi_2$ is 0.1-5 ns. However, the specific value of the time difference $\gamma$ can be determined experimentally.

During the second phase (of the first cycle $Cyc_1$) $P_{b,1}$, a second switching signal $\phi_3$ connects the photodetector 136 to the charge integrator circuit 154. It is possible to use the same switching signal (i.e., $\phi_2=\phi_3$) to connect the photodetector 136 to the low-impedance dump voltage $V_{rt}$ and to the charge integrator circuit 154. However, as the width of the pulses will be on the order of 1-10 ns, the propagation delay of light and electrical signals should not be taken into account. Consequently, it is more flexible to use two separate switching signals $\phi_2$, $\phi_3$ for the two connections, since this arrangement permits phase adjustment.

There is a short delay ε between the falling edge of the first switching signal $\phi_2$ and the rising edge of the second switching signal $\phi_3$. This is not a particularly critical parameter. As both switches $S^a$ and $S_b$ are open-circuited, photogenerated electrons will be stored in the photodetector 136 and converted into charge on the feedback capacitor $C_{fb}$ as soon as $\phi_3$ goes high and the photodetector 136 is connected to the charge integrator circuit 154.

Successive operational cycles of the improved fluorescence biosensor are performed in a similar manner to the first cycle. In other words, the first phase $p_{a,2}$ of the second cycle $Cyc_2$ sees the stimulating light source 132 being switched on and the photodetector 136 being connected to the dump voltage $V_{rt}$. Similarly, the second phase $p_{b,2}$ of the second cycle Cyc2 sees the stimulating light source 132 being switched off and the photodetector 136 being disconnected from the dump voltage $V_{rt}$ and reconnected to the charge integrator circuit 154.

Referring to the final trace $V_{out}$ in FIG. 6, during the second phase $p_{b,1}$ of the first cycle $Cyc_1$, the output voltage $V_{out}$ of the charge integrator 154 increases to $\delta V$ in a similar manner to a conventional prior art fluorescence biosensor. However, in contrast with conventional prior art fluorescence biosensors, after the end of the second phase $p_{b,1}$ of the first cycle $Cyc_1$, the fluorescence biosensor 100 performs cycles $Cyc_2$ and $Cyc_3$ without resetting the charge integrator 154. Hence, electrons generated in the photodetector 136 by the incident fluorescence photons cause the output voltage $V_{out}$ of the fluorescence biosensor 100 to continually increase.

As an aside, since the fluorescence biosensor 100 essentially relies on the accumulation of charge over a number of operational cycles, it is important that the charge injected by the opening and closing of the switches $S_a$ and $S_b$ is minimized. This is a well-known problem with a well-known approach as shown in FIG. 7, wherein this approach comprises the steps of:

(a) using CMOS (i.e., NMOS and PMOS) switching transistors (N1, P2) in parallel; and (b) using dummy transistors (N1, N3, P1, P3) with opposing clock phases.

Figure 7:
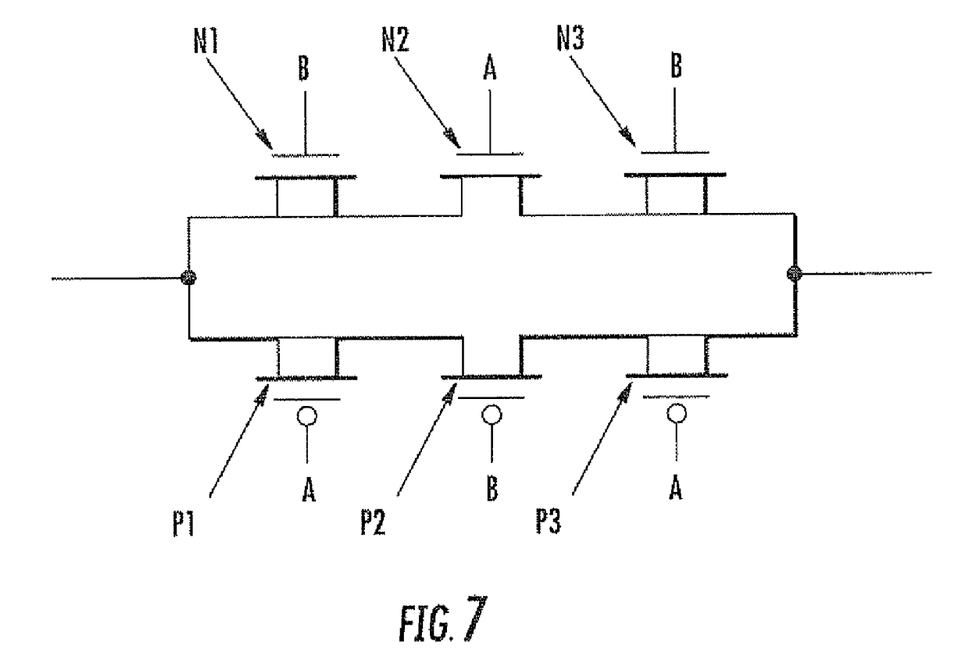
FIG. 7 is a circuit diagram of a CMOS switch with charge cancellation used in the fluorescence biosensor shown in FIG. 5.

Referring to FIG. 7, signal A is of opposite polarity to signal B and the sizes (width and length) of the switching transistors P2 and N2 are equal. In this case, the lengths of the dummy transistors (N1, N3, P1, P3) are half the lengths of the switching transistors (N2, P2).

Referring to FIG. 5, it is also preferable to use the same voltage for the non-inverting input of the charge amplifier 156 as that used for the sink of photogenerated electrons during the first phase of each cycle (i.e., the dump voltage $V_{rt}$). As the fluorescence biosensor's photodetector 136 is held at this potential during the second phase of each cycle (as a result of the negative feedback applied to the charge amplifier 156), this also reduces any charge injection into the photodetector 136.

While in theory the operational cycles of the fluorescence biosensor 100 can be continued indefinitely (and the photogenerated electrons accumulated therewithin), in practice, the number of such operational cycles is limited by the photostability of the fluorescent labels, support, biological macromolecules and/or analytes.

It will be appreciated that the fluorescence biosensor has a wide range of applications including clinical diagnostic systems, food testing and quality assurance systems, environmental testing systems and pharmaceutical testing systems to aid in drug development and discovery. Alterations and modifications may be made to the above without departing from the scope of the invention.

That which is claimed:

1. A fluorescence detector comprising:
   a light source for emitting radiation on at least one fluorescing species;
   a charge integrating circuit;
   a charge disposal device;
   a photodetector to detect fluorescent radiation from the at least one fluorescing species and being switchable between said charge integrating circuit and said charge disposal device; and
   a controller cooperating with said light source and said photodetector to cyclically activate said light source for a first period of time and switch said photodetector to said charge disposal device for the first period of time, and to deactivate said light source and switch said photodetector to the charge integrating circuit for a second period of time after the first period of time;
   said controller not resetting said charge integrating circuit from at least one cycle to the next.

2. The fluorescence detector of claim 1 wherein said controller is to switch said photodetector to said charge integrating circuit in a time range of 0.1 ns to 5 ns after the first period of time.

3. The fluorescence detector of claim 1 further comprising circuitry to minimize a charge injected into said charge integrating circuit by switching said photodetector from said charge disposal device to said charge integrating circuit.

4. The fluorescence detector of claim 1, wherein the fluorescence detector is integrated with the at least one fluorescing species to define a fluorescence biosensor, and the at least one fluorescing species comprises a biological macromolecule.

5. The fluorescence detector of claim 1 wherein the fluorescence detector is integrated with the at least one fluorescing species to define a fluorescence biosensor, and the at least one fluorescing species comprises a fluorescently labeled biological macromolecule.

6. The fluorescence detector of claim 1 wherein said light source, charge integrating circuit, charge disposal device, photodetector, and controller define a clinical diagnostic system.

7. The fluorescence detector of claim 1 wherein said light source, charge integrating circuit, charge disposal device, photodetector, and controller define a food testing system.

8. The fluorescence detector of claim 1 wherein said light source, charge integrating circuit, charge disposal device, photodetector, and controller define a pharmaceutical testing system.

9. A fluorescence detector comprising:
   a light source for emitting radiation on at least one fluorescing species;
   a charge integrating circuit;
   a charge disposal device;
   a photodetector to detect fluorescent radiation from the at least one fluorescing species and being switchable between said charge integrating circuit and said charge disposal device;
   a reducing circuit to reduce a charge injected into said charge integrating circuit by switching said photodetector from said charge disposal device to said charge integrating circuit; and
   a controller cooperating with said light source and said photodetector to cyclically activate said light source for a first period of time and switch said photodetector to said charge disposal device for the first period of time, and to deactivate said light source and switch said photodetector to the charge integrating circuit for a second period of time after the first period of time;

said controller not resetting said charge integrating circuit from at least one cycle to the next.

10. The fluorescence detector of claim 9 wherein said light source, charge integrating circuit, charge disposal device, photodetector, reducing circuit, and controller define a pharmaceutical testing system.

* * * * *

UNITED STATES PATENT AND TRADEMARK OFFICE
CERTIFICATE OF CORRECTION

PATENT NO. : 7,541,176 B2
APPLICATION NO. : 11/677765
DATED : June 2, 2009
INVENTOR(S) : Jeffrey Raynor It is certified that error appears in the above-identified patent and that said Letters Patent is hereby corrected as shown below:

Column 2, Line 9    Delete: "wavelength $\lambda^1$"
                    Insert: -- wavelength $\lambda_1$ --

Column 2, Line 20   Delete: "wavelength $\lambda^2$"
                    Insert: -- wavelength $\lambda_2$ --

Column 2, Line 21   Delete: "$\lambda^1 < \lambda^2$"
                    Insert: -- $\lambda_1 < \lambda_2$ --

Column 2, Line 34   Delete: "radiation $\lambda^2$"
                    Insert: -- radiation $\lambda_2$ --

Column 7, Line 4    Delete: "switches $S^a$"
                    Insert: -- switches $S_a$ --

Column 7, Line 38   Delete: "sistors (N1, P2)"
                    Insert: -- sistors (N2, P2) --

Signed and Sealed this

Eighth Day of September, 2009

David J. Kappos
*Director of the United States Patent and Trademark Office*